United States Patent [19]

Takano et al.

[11] Patent Number: 5,043,094
[45] Date of Patent: Aug. 27, 1991

[54] OPTICALLY ACTIVE BISARYL COMPOUND

[75] Inventors: Seiichi Takano, Izumi; Kunio Ogasawara, Sendai; Toshihiro Shibata, Omiya; Norio Kurosawa, Urawa, all of Japan

[73] Assignee: Adeka Argus Chemical Co., Ltd., Tokyo, Japan

[21] Appl. No.: 326,539

[22] Filed: Mar. 20, 1989

[30] Foreign Application Priority Data

Apr. 6, 1988 [JP] Japan .................................. 63-84576

[51] Int. Cl.$^5$ ...................... C09K 19/34; C09K 19/32; C09K 19/20
[52] U.S. Cl. .......................... 252/299.61; 252/299.62; 252/299.64
[58] Field of Search ............ 252/299.01, 299.1, 299.6, 252/299.61, 299.62, 299.63, 299.64, 299.65, 299.66, 299.67, 299.5; 350/350 R, 350 S, 351

[56] References Cited

U.S. PATENT DOCUMENTS 4,400,293  8/1983  Römer et al. .................. 252/299.63
4,514,045  4/1985  Huffman et al. .................... 350/351
4,650,600  3/1987  Heppke et al. ................. 252/299.01

Primary Examiner—John S. Maples
Assistant Examiner—Shean C. Wu
Attorney, Agent, or Firm—Frishauf, Holtz, Goodman & Woodward

[57] ABSTRACT

An optically active bisaryl compound represented by the general formula (I):

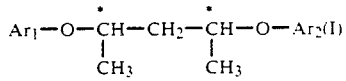

wherein $Ar_1$ and $Ar_2$ represent each a phenyl, naphthyl, biphenyl or pyrimidylphenyl group optionally substituted with an alkyl, alkoxy, cyano or cycloalkyl group or a halogen atom, and * represents an asymmetric carbon atom, which can give a cholesteric phase of a short helical pitch when added to nematic liquid crystals useful as a component of a liquid crystal mixture for a display device.

26 Claims, No Drawings

OPTICALLY ACTIVE BISARYL COMPOUND

BACKGROUND OF THE INVENTION

1. Field of the Invention

This invention relates to a specific optically active compound. More particularly, it relates to an optically active bisaryl compound.

2. Description of the Prior Art

Liquid crystals have been employed in various electrooptical devices. Recently they have been applied to display devices of, for example, watches, electric calculaters and automobile panels. Most of the liquid crystal display devices which are practically employed today are those prepared by taking advantage of the dielectric alignment effects of twistnematic liquid crystals or cholesteric liquid crystals. Recently it has been often attempted to develop liquid crystal display systems other than those described above. Examples of these new systems include STN systems and cholesteric/nematic phase transition systems.

Each liquid crystal composition to be used in such a liquid crystal display device as described above is adjusted in such a manner as to achieve the aimed helical pitch by introducing an optically active group into nematic liquid crystals or by adding an optically active substance thereto. For example, there is known a Shiff base liquid crystal obtained from p-alkoxybenzaldehyde and (+)-p-amino-2-methylbutylbenzene. An example of the optically active substance to be added is 4-(2-methylbutyloxy)-4'-cyanobiphenyl. However it is necessary to use a disadvantageously large amount of this compound in order to achieve the aimed properties, since it has a long twist pitch of cholesteric liquid crystals.

SUMMARY OF THE INVENTION

Under these circumstances, the present inventors have conducted extensive studies in order to find a compound which is capable of giving a cholesteric phase of a short helical pitch when added to nematic liquid crystals useful as a component of a liquid crystal mixture for a display device. As a result, they have found that an optically active compound represented by the following general formula (I) is highly suitable for achieving the above object:

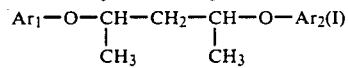

wherein $Ar_1$ and $Ar_2$ represent each a phenyl, naphthyl, biphenyl or pyrimidylphenyl group optionally substituted with an alkyl, alkoxy, cyano or cycloalkyl group or a halogen atom, and * represents an asymmetric carbon atom.

The optically active bisaryl compound of the present invention represented by the above general formula (I) can give a cholesteric phase of a short helical pitch, when added to nematic liquid crystals useful as a component of a liquid crystal mixture for a display device.

DETAILED DESCRIPTION OF THE INVENTION

Examples of the alkyl group in the compound of the present invention of the general formula (I) include methyl, ethyl, propyl, isopropyl, butyl, sec-butyl, isobutyl, ter-butyl, hexyl, octyl, 2-ethylhexyl, decyl and benzyl groups.

Examples of the alkoxy group therein include methoxy, ethoxy, propoxy, isopropoxy, butoxy, hexyloxy, octyloxy and decyloxy groups.

The compound of the present invention of the general formula (I) may be readily prepared by, for example, reacting phenol, naphthol, phenylphenol or phenylpyrimidine with tosylate of 2,4-pentanediol in the presence of a catalyst such as sodium hydride.

To further illustrate the present invention, and not by way of limitation, the following Examples will be given.

Example 1: Synthesis of (S,S)-2,4-diphenoxypentane 0.21 g of 55 % sodium hydride was mixed with 5 ml of dimethylformamide (DMF) and a solution of 0.38 g of phenol in 2 ml of DMF was added dropwise thereto under ice-cooling. After the completion of the addition, the resulting mixture was stirred at room temperature for one hour. Then a solution of 0.91 g of optically active (R,R)-2,4-pentanediol ditosylate in 2 ml of DMF was added dropwise thereto and the obtained mixture was stirred at 90° C. for two hours. After cooling, the reaction mixture was poured into 100 ml of ice/water, extracted with ethyl ether, dried and freed of the solvent. The residue was then purified by silica gel column chromatography with the use of a mixture of n-hexane with ethyl acetate (97/3) as a developing solvent. Thus 0.22 g of optically active (S,S)-2,4-diphenoxypentane was obtained.

This product showed the following characteristic absorptions in infrared spectroscopy, which proved that it was the aimed compound.

$2970 cm^{-1}$ (s), $2920 cm^{-1}$ (m), $1595 cm^{-1}$ (s), $1580 cm^{-1}$ (s), $1490 cm^{-1}$ (vs), $1235 cm^{-1}$ (vs) $750 cm^{-1}$ (s)

Example 2: Synthesis of (S,S)-2,4-bis(4'-phenylphenoxy)pentane

The procedure of Example 1 was repeated except that the phenol was replaced with 0.68 g of 4-phenylphenol. The crude product thus obtained was recrystallized from methanol to thereby give 0.69 g of optically active (S,S)-2,4-bis(4'-phenylphenoy)pentane (m.p.: 80.7° C.).

This product showed the following characteristic absorptions in infrared spectroscopy, which proved that it was the aimed compound.

$2960 cm^{-1}$ (w), $1605 cm^{-1}$ (s), $1515 cm^{-1}$ (s) $1480 cm^{-1}$ (vs), $830 cm$ (s) $755 cm$ (vs)

Example 3: Synthesis of (S,S)-2,4-bis(4'-methylphenoxy)pentane 0.21 g of 55 % sodium hydride was mixed with 5 ml of DMF and a solution of 0.43 g of p-cresol in 2 ml of DMF was added dropwise thereto under ice-cooling. After the completion of the addition, the resulting mixture was stirred at room temperature for one hour. Then a solution of 0.91 g of optically active (R,R)-2,4-pentanediol ditosylate in 2 ml of DMF was added dropwise thereto and the obtained mixture was stirred at 90° C. for three hours. After cooling, the reaction mixture was poured into 100 ml of ice/water, extracted with ethyl ether, dried and freed of the solvent. The residue was then purified by silica gel column chromatography with the use of a mixture of n-hexane with ethyl acetate (97/3) as a developing solvent. Thus 0.28 g of optically active (S,S)-2,4-bis(4'-methylphenoxy)pentane was obtained.

This product showed the following characteristic absorptions in infrared spectroscopy, which proved that it was the aimed compound.

2970cm$^{-1}$ (m), 2920cm$^{-1}$ (m), 1610cm$^{-1}$ (m) 1580cm$^{-1}$ (w), 1505cm$^{-1}$ (vs), 1235cm$^{-1}$ (vs) 820cm$^{-1}$ (m)

Example 4: Synthesis of (S,S)-2,4-bis(4'-ethylphenoxy)pentane

The procedure of Example 3 was repeated except that the p-cresol was replaced with 0.67 g of 4-ethylphenol. The crude product thus obtained was then purified by silica gel column chromatography with the use of a mixture of n-hexane with ethyl acetate (95/5) as a developing solvent. Thus 0.39 g of optically active (S,S)-2,4-bis(4'-ethylphenoxy)pentane was obtained.

This product showed the following characteristic absorptions in infrared spectroscopy, which provided that it was the aimed compound.

2975cm$^{-1}$ (m), 1610cm$^{-1}$ (s), 1580cm$^{-1}$ (m) 1508cm$^{-1}$ (s), 1230cm$^{-1}$ (s), 830cm$^{-1}$ (s)

Example 5: Synthesis of (S,S)-2,4-bis(4'-methoxyphenoxy)pentane 0.33 g of 55 % sodium hydride was mixed with 15 ml of DMF and a solution of 0.63 g of p-methoxyphenol in 2 ml of DMF was added dropwise thereto under ice-cooling. After the completion of the addition, the resulting mixture was stirred at room temperature for one hour. Then a solution of 0.95 g of optically active (R,R)-2,4-pentanediol ditosylate in 3 ml of DMF was added dropwise thereto and the obtained mixture was stirred at 90° C. for two hours. After cooling, the reaction mixture was poured into 100 ml of ice/water, extracted with ethyl ether, dried and freed of the solvent. The residue was then purified by silica gel column chromatography with the use of a mixture of n-hexane with ethyl acetate (9/1) as a developing solvent. Thus 0.29 g of optically active (S,S)-2,4-bis(4'-methoxyphenoxy)pentane was obtained.

This product showed the following characteristic absorptions in infrared spectroscopy, which proved that it was the aimed compound.

2970cm$^{-1}$ (m), 2830cm$^{-1}$ (w), 1585cm$^{-1}$ (w) 1500cm$^{-1}$ (vs), 1225cm$^{-1}$ (vs), 1040cm$^{-1}$ (s) 830cm$^{-1}$ (m)

Example 6: Synthesis of (S,S)-2,4-bis(4'-ethoxyphenoxy)pentane

The procedure of Example 5 was repeated except that the 4-methoxyphenol was replaced with 0.69 g of 4-ethoxyphenol. The crude product thus obtained was then purified by silica gen column chromatography with the use of a mixture of n-hexane with ethyl acetate (95/5) as a developing solvent. Thus 0.41 g of optically active (S,S)-2,4-bis(4'-ethoxyphenoxy)pentane was obtained.

This product showed the following characteristic absorptions in infrared spectroscopy, which proved that it was the aimed compound.

1970cm$^{-1}$ (s), 1910cm$^{-1}$ (m), 1585cm$^{-1}$ (w) 1500cm$^{-1}$ (vs), 1220cm$^{-1}$ (vs), 820cm$^{-1}$ (m)

Example 7: Synthesis of (S,S)-2,4-bis[4'-(4''-methoxyphenyl)phenoxy]pentane 0.21 g of 55 % sodium hydride was mixed with 5 ml of DMF and a solution of 0.62 g of 4-(4'methoxyphenyl)phenol in 2 ml of DMF was added dropwise thereto under ice-cooling. After the completion of the addition, the resulting mixture was stirred at room temperature for two hours. Then a solution of 0.91 g of optically active (R,R)-2,4-pentanediol ditosylate in 2 ml of DMF was added dropwise thereto and the obtained mixture was stirred at 90° C. for three hours. After cooling, the reaction mixture was poured into 100 ml of ice/water, extracted with ethyl ether, dried and freed of the solvent. The residue was then recrystallized from ethanol. Thus 0.16 g of optically active (S,S)-2,4-bis[4'-(4''-methoxyphenyl)phenoxy]pentane was obtained (m.p.: 164.5° C.).

This product showed the following characteristic absorptions in infrared spectroscopy, which proved that it was the aimed compound.

2970cm$^{-1}$ (m), 2820cm$^{-1}$ (w), 1600cm$^{-1}$ (s) 1495cm$^{-1}$ (vs), 1460cm$^{-1}$ (w), 1235cm$^{-1}$ (vs) 820cm$^{-1}$ (s)

Example 8: Synthesis of (S,S)-2,4-bis(4'-cyclohexylphenoxy)pentane

The procedure of Example 7 was repeated except that the 4-(4'-methoxyphenyl)phenol was replaced with 0.70 g of 4-cyclohexylphenol. The crude product thus obtained was purified by column chromatography with the use of a mixture of n-hexane with ethyl acetate (97/3) as a developing solvent. Thus optically active (S,S)-2,4-bis(4'-cyclohexylphenoy)pentane was obtained.

This product showed the following characteristic absorptions in infrared spectroscopy, which proved that it was the aimed compound.

2910cm$^{-1}$ (s), 2840cm$^{-1}$ (m), 1605cm$^{-1}$ (m) 1575cm$^{-1}$ (w), 1505cm$^{-1}$ (s), 1235cm$^{-1}$ (s) 820cm$^{-1}$ (m)

Example 9: Synthesis of (S,S)-2,4-bis(4'-chlorophenoxy)pentane 0.21 g of 55 % sodium hydride was mixed with 5 ml of DMF and a solution of 0.52 g of 4-chlorophenol in 2 ml of DMF was added dropwise thereto under ice-cooling. After the completion of the addition, the resulting mixture was stirred at room temperature for ore hour. Then a solution of 0.91 g of optically active (R,R)-2,4-pentanediol ditosylate in 2 ml of EMF was added dropwise thereto and the obtained mixture was stirred at 90° C. for three hours. After cooling, the reaction mixture was poured into 100 ml of ice/water, extracted with ethyl ether, dried and freed of the solvent. The residue was then purified by silica gel column chromatography with the use of a mixture of n-hexane with ethyl acetate (97/3) as a developing solvent. Thus 0.30 g cf optically active (S,S)-2,4-bis (4'-chlorophenoxy)pentane was obtained.

This product showed the following characteristic absorptions in infrared spectroscopy, which proved that it was the aimed compound.

2980cm$^{-1}$ (s), 2925cm$^{-1}$ (m), 1595cm$^{-1}$ (s) 1590cm$^{-1}$ (m), 1490cm$^{-1}$ (vs), 1240cm$^{-1}$ (vs) 825cm$^{-1}$ (s), 670cm$^{-1}$ (s)

Example 10: Synthesis of (S,S)-2,4-bis(3'-chlorophenoxy)pentane

The procedure of Example 9 was repeated except that the 4-chlorophenol was replaced with 0.52 g of 3-chlorophenol. Thus 0.33 g of optically active (S,S)-2,4-bis(3'chlorophenoxy)pentane was obtained.

This product showed the following characteristic absorptions in infrared spectroscopy, which proved that it was the aimed compound.

2980cm$^{-1}$ (m), 2220cm$^{-1}$ (s), 1605cm$^{-1}$ (vs) 1570cm$^{-1}$ (w), 1500cm$^{-1}$ (s), 1255cm$^{-1}$ (vs) 840cm$^{-1}$ (s)

Example 11: Synthesis of (S,S)-2,4-bis(4'-cyanophenoxy)pentane 0.21 g of 55% sodium hydride was mixed with 5 ml of DMF and a solution of 0.49 g of 4-cyanophenol in 2 ml of DMF was added dropwise thereto under ice-cooling. After the completion of the addition, the resulting mixture was stirred at room temperature for three hours. Then a solution of 0.91 g of optically active (R,R)-2,4-pentanediol ditosylate in 2 ml of DMF was added dropwise thereto and the obtained mixture was stirred at 90° C. for one hour. After cooling, the reaction mixture was poured into 100 ml of ice/water, extracted with ethyl ether, dried and freed of the solvent. The residue was then purified by silica gel column chromatography with the use of a mixture of n-hexane with ethyl acetate (97/3) as a developing solvent. Thus 0.40 g of optically active (S,S)-2,4-bis (4'-cyanophenoxy)pentane was obtained.

This product showed the following characteristic absorptions in infrared spectroscopy, which proved that it was the aimed compound.

2980cm$^{-1}$ (m), 2220cm$^{-1}$ (s), 1650cm$^{-1}$ (vs) 1570cm$^{-1}$ (w), 1500cm$^{-1}$ (s), 1255cm$^{-1}$ (vs) 840cm$^{-1}$ (s)

Example 12: Synthesis of (S,S)-2,4-bis[4'-(4''-cyanophenyl) phenoxy]pentane

The procedure of Example 11 was repeated except that the 4-cyanophenol was replaced with 0.60 g of 4-(4'-cyanophenyl)phenol. The crude product thus obtained was then recrystallized from ethyl alcohol. Thus 0.49 g of optically active (S,S)-2,4-bis[4'-(4''-cyanophenyl)phenoxy]pentane was obtained (m.p.: 139.5° C.).

This product showed the following characteristic absorptions in infrared spectroscopy, which proved that it was the aimed compound.

2970cm$^{-1}$ (w), 2220cm$^{-1}$ (s), 1605cm$^{-1}$ (s) 1580cm$^{-1}$ (w), 1490cm$^{-1}$ (vs), 1240cm$^{-1}$ (s) 820cm$^{-1}$ (s)

Example 13: Synthesis of (S,S)-2,4-bis(β-naphthoxy)pentane 0.21 g of 55% sodium hydride was mixed with 5 ml of DMF and a solution of 0.58 g of β-naphtol in 2 ml of DMF was added dropwise thereto under ice-cooling. After the completion of the addition, the resulting mixture was stirred at room temperature for three hours. Then a solution of 0.91 g of optically active (R,R)-2,4-pentanediol ditosylate in 2 ml of DMF was added dropwise thereto and the obtained mixture was stirred at 90° C. for three hours. After cooling, the reaction mixture was poured into 100 ml of ice/water, extracted with ethyl ether, dried and freed of the solvent. The residue was then purified by silica gel column chromatography with the use of a mixture of n-hexane with ethyl acetate (97/3) as a developing solvent. Thus 0.48 g of optically active (S,S)-2,4-bis (β-naphthozy)pentane was obtained.

This product showed the following characteristic absorptions in infrared spectroscopy, which proved that it was the aimed compound.

3050cm$^{-1}$ (m), 2970cm$^{-1}$ (s), 1625cm$^{-1}$ (s) 1600cm$^{-1}$ (s), 1505cm$^{-1}$ (s), 1465cm$^{-1}$ (s) 1255cm$^{-1}$ (s), 1210cm$^{-1}$ (s)

Example 14: Synthesis of (S,S)-2,4-bis[4'-(5''-hexylpyrimidin-2''-yl) phenoxy]pentane 0.21 g of 55% sodium hydride was mixed with 5 ml of DMF and a solution of 1.03 g of 4-(5'-hexylpyrimidin-2'-yl)-phenol in 3 ml of DMF was added dropwise thereto under ice-cooling. After the completion of the addition, the resulting mixture was stirred at room temperature for one hour. Then a solution of 0.91 g of optically active (R,R)-2,4-pentanediol ditosylate in 2 ml of DMF was added dropwise thereto and the obtained mixture was stirred at 90° C. for three hours. After cooling, the reaction mixture was poured into 100 ml of ice/water, extracted with ethyl ether, dried and freed of the solvent. The residue was then recrystallized from ethyl alcohol. Thus 0.84 g of optically active (S,S)-2,4-bis[4'-(5''-hexylpyrimidin-2''-yl) phenoxy]pentane was obtained (m.p.: 59.5° C.).

This product showed the following characteristic absorptions in infrared spectroscopy, which proved that it was the aimed compound.

2920cm$^{-1}$ (s), 2840cm$^{-1}$ (s), 1605cm$^{-1}$ (s) 1580cm$^{-1}$ (s), 1535cm$^{-1}$ (m), 1510cm$^{-1}$ (m) 1425cm$^{-1}$ (vs), 1250cm$^{-1}$ (s), 1235cm$^{-1}$ (s) 1170cm$^{-1}$ (s)

Example 15: Synthesis of (S,S)-2-(4'-phenylphenoxy)-4-[4'-(5''-decylpyrimidin-2''-yl) phenoxy]pentane 0.26 g of 55% sodium hydride was mixed with 5 ml of DMF and 0.85 g of 4-phenylphenol was added dropwise thereto. After the completion of the reaction, 1.42 g of optically active (R,R)-2,4-pentanediol monotosylate in 5 ml of DMF was added dropwise thereto. After reacting at 90° C. for three hours, the reaction mixture was treated in a conventional manner. Then it was purified by silica gel column chromatography with the use of a mixture of n-hexane with ethyl acetate (7/3) as a developing solvent. Thus 0.77 g of optically active (S,S)-2-(4'-phenylphenoxy)pentan-4-ol was obtained. Separately, 0.08 g of 55% sodium hydride was mixed with 3 ml of DMF and a solution of 0.49 g of 5-n-decylpyrimidine in 3 of DMF was added dropwise thereto. Then a solution of 0.71 g of the (S,S)-2-(4'-phenylphenoxy)pentane-4-ol tosylate obtained above in 3 ml of DMF was added dropwise thereto and the obtained mixture was stirred at 90° C. for five hours. After cooling, the reaction mixture was poured into 100 ml of ice/water, extracted with ethyl ether, dried and freed of the solvent. The residue was then purified by silica gel column chromatography with the use of a mixture of n-hexane with ethyl acetate (8/2) as a developing solvent. Thus 0.82 g of optically active (s,S)-2-(4'-phenylphenoxy)-4-[4'-(5''-dicylpyrimidin-2''-yl)phenoxy]pentane was obtained.

This product showed the following characteristic absorptions in infrared spectroscopy, which proved that it was the aimed compound.

2910cm$^{-1}$ (s), 2840cm$^{-1}$ (m), 1600cm$^{-1}$ (s), 1580cm$^{-1}$ (s), 1420cm$^{-1}$ (vs), 1240cm$^{-1}$ (vs), 1170cm$^{-1}$ (vs), 760cm$^{-1}$ (m)

The following Table 1 summarizes the structural formulae of the compounds of the present invention synthesized in the above Examples 1 to 15.

TABLE 1

Compound of each Example:

$$Ar_1-O-\overset{*}{C}H-CH_2-\overset{*}{C}H-O-Ar_2$$
$$\quad\quad\quad\;\;|\quad\quad\quad\;\;|$$
$$\quad\quad\quad CH_3\quad\quad CH_3$$

| Example No. | Ar$_1$ | Ar$_2$ |
|---|---|---|
| 1 | —⟨phenyl⟩ | —⟨phenyl⟩ |
| 2 | —⟨phenyl⟩—⟨phenyl⟩ | —⟨phenyl⟩—⟨phenyl⟩ |
| 3 | —⟨phenyl⟩—CH$_3$ | —⟨phenyl⟩—CH$_3$ |
| 4 | —⟨phenyl⟩—C$_2$H$_5$ | —⟨phenyl⟩—C$_2$H$_5$ |
| 5 | —⟨phenyl⟩—O—CH$_3$ | —⟨phenyl⟩—O—CH$_3$ |
| 6 | —⟨phenyl⟩—O—C$_2$H$_5$ | —⟨phenyl⟩—O—C$_2$H$_5$ |
| 7 | —⟨phenyl⟩—⟨phenyl⟩—OCH$_3$ | —⟨phenyl⟩—⟨phenyl⟩—OCH$_3$ |
| 8 | —⟨phenyl⟩—⟨cyclohexyl-H⟩ | —⟨phenyl⟩—⟨cyclohexyl-H⟩ |
| 9 | —⟨phenyl⟩—Cl | —⟨phenyl⟩—Cl |
| 10 | —⟨phenyl with Cl meta⟩ | —⟨phenyl with Cl meta⟩ |
| 11 | —⟨phenyl⟩—CN | —⟨phenyl⟩—CN |

TABLE 1-continued

Compound of each Example:

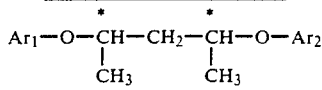

| Example No. | Ar₁ | Ar₂ |
|---|---|---|
| 12 |  | 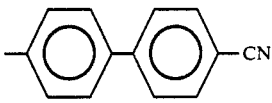 |
| 13 | 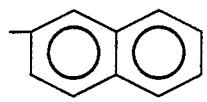 | 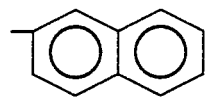 |
| 14 | 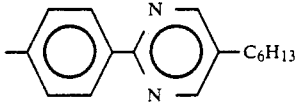 | 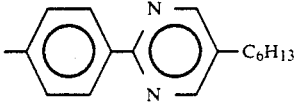 |
| 15 | 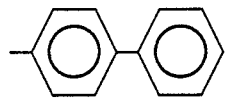 | 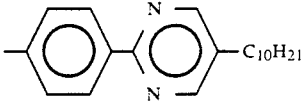 |

Referential Example

2% by weight of each compound of the above Examples 1 to 15 was mixed with typical nematic liquid crystals ZLI-1565 manufactured by Merck. The pitch of the obtained mixture was determined at 30° C. and 60° C. in a Kano wedge-shaped cell. Table 2 shows the results.

TABLE 2

| Compound | Pitch (μm) at 30° C. | at 60° C. |
|---|---|---|
| none | — | — |
| Ex. 1 | 6.5 | 8.0 |
| Ex. 2 | 3.5 | 3.7 |
| Ex. 3 | 5.1 | 6.4 |
| Ex. 4 | 7.1 | 8.6 |
| Ex. 5 | 3.3 | 3.9 |
| Ex. 6 | 4.7 | 6.0 |
| Ex. 7 | 4.5 | 4.6 |
| Ex. 8 | 10.5 | 10.7 |
| Ex. 9 | 5.8 | 7.0 |
| Ex. 10 | 16.1 | 18.3 |
| Ex. 11 | 7.2 | 8.6 |
| Ex. 12 | 3.9 | 3.7 |
| Ex. 13 | 3.9 | 4.8 |
| Ex. 14 | 4.6 | 5.1 |
| Ex. 15 | 4.5 | 5.0 |

Table 2 obviously indicates that the compound of the present invention is highly useful as a chiral compound capable of giving any desired pitch to a liquid crystal composition.

What is claimed is:

1. An optically active bisaryl compound of a formula (I):

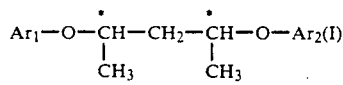

wherein Ar₁ and Ar₂ are each a phenyl, naphthyl, biphenyl or pyrimidylphenyl group unsubstituted or substituted with an alkyl or alkoxy group having 1 to 10 carbon atom, cyano or cyclohexyl group or a halogen atom, and * represents an asymmetric carbon atom.

2. The optically active bisaryl compound as set forth in claim 1, wherein Ar₁ and Ar₂ are each a phenyl group.

3. The optically active bisaryl compound as set forth in claim 1, wherein Ar₁ and Ar₂ are each a biphenyl group.

4. The optically active bisaryl compound as set forth in claim 1, wherein Ar₁ and Ar₂ are each an alkylphenyl group.

5. The optically active bisaryl compound as set forth in claim 1, wherein Ar₁ and Ar₂ are each an alkoxyphenyl group.

6. The optically active bisaryl compound as set forth in claim 1, wherein Ar₁ and Ar₂ are each a cyanophenyl group.

7. The optically active bisaryl compound as set forth in claim 1, wherein Ar₁ and Ar₂ are each a cyanobiphenyl group.

8. A nematic liquid crystal composition comprising nematic crystals and an optically active bisaryl compound as set forth in claim 1.

9. The optically active bisaryl compound as set forth in claim 1, wherein Ar₁ and Ar₂ are each a phenyl, naphthyl, biphenyl or pyrimidylphenyl group substituted by an alkyl selected from the group consisting of methyl, ethyl, propyl, isopropyl, butyl, sec-butyl, isobutyl, ter-butyl, hexyl, octyl, 2-ethylhexyl, and decyl.

10. The optically active bisaryl compound as set forth in claim 1, wherein Ar₁ and Ar₂ are each a pehnyl, naphthyl, biphenyl or pyrimidylphenyl group substituted by an alkoxy selected form the group consisting of methoxy, ethoxy, propoxy, isopropoxy, butoxy, hexyloxy, octyloxy and decyloxy.

11. The optically active bisaryl compound as set forth in claim 1, wherein the compound is (S,S)-2,4-diphenoxypentane.

12. The optically active bisaryl compound as set forth in claim 1, wherein the compound is (S,S)-2,4-bis(4'-methylphenoxy)pentane.

13. The optically active bisaryl compound as set forth in claim 1, wherein the compound is (S,S)-2,4-bis(4'-methylphenoxy)pentane.

14. The optically active bisaryl compound as set forth in claim 1, wherein the compound is (S,S)-2,4-bis(4'-ethylphenoxy)pentane.

15. The optically active bisaryl compound as set forth in claim 1, wherein the compound is (S,S)-2,4-bis(4'-methoxyphenoxy)pentane.

16. The optically active bisaryl compound as set forth in claim 1, wherein the compound is (S,S)-2,4-bis(4'-ethoxyphenoxy)pentane 17. The optically active bisaryl compound as set forth in claim 1, wherein the compound is (S,S)-2,4-bis(4'-(4''-methoxyphenyl) phenoxy)pentane.

18. The optically active bisaryl compound as set forth in claim 1, wherein the compound is (S,S)-2,4-bis(4'-cyclohexylphenoxy) pentane.

19. The optically active bisaryl compound as set forth in claim 1, wherein the compound is (S,S)-2,4-bis (4'-chlorophenoxy) pentane.

20. The optically active bisaryl compound as set forth in claim 1, wherein the compound is (S,S)-2,4-bis(3'-chlorophenoxy)pentane.

21. The optically active bisaryl compound as set forth in claim 1, wherein the compound is (S,S)-2,4-bis(4'-cyanophenoxy)pentane.

22. The optically active bisaryl compound as set forth in claim 1, wherein the compound is (S,S)-2,4-bis(4'(4''-cyanophenyl) phenoxy)pentane.

23. The optically active bisaryl compound as set forth in claim 1, wherein the compound is (S,S)-2,4-bis($\beta$-naphthoxy)pentane.

24. The optically active bisaryl compound as set forth in claim 1, wherein the compound is (S,S)-2,4-bis(4'-(5''-hexylpyrimidin-2-yl) phenoxy)pentane.

25. The optically active bisaryl compound as set forth in claim 1, wherein the compound is (S,S)-2-(4'-phenylphenoxy)-4-(4'-(5''-decylpyrimidin-2''-yl)phenoxy)pentane.

26. The nematic liquid crystal composition as set forth in claim 8, wherein the optically active bisaryl compound is selected from the group consisting of (S,S)-2,4-diphenoxypentane, (S,S)-2,4-bis(4'-phenylphenoxy)pentane, (S,S)-2,4-bis(4'-methylphenoxy) pentane, (S,S)-2,4-bis(4'-ethylphenoxy)pentane, (S,S)2,4-bis(4'-methoxyphenoxy)pentane, (S,S)-2,4-bis(4'-ethoxyphenoxy) pentane, (S,S)-2,4-bis(4-(4''-methoxyphenyl) phenoxy)pentane, (S,S)-2,4-bis(4'-cyclohexylphenoxy) pentane, (S,S)-2,4-bis (4'-chlorophenoxy) pentane, (S,S)-2,4-bis(3'-chlorophenoxy)pentane, (S,S)-2,4-bis(4'-cyanophenoxy)pentane, (S,S)-2,4-bis(4'-(4''-cyanophenyl) phenoxy)pentane, (S,S)-2,4-bis($\beta$-naphthoxy)pentane, (S,S)-2,4-bis(4'(5''-hexylpyrimidin-2''-yl)phenoxy)pentane, and (S,S)-2-(4'-phenylphenoxy)-4-(4'(5''-decylpyrimidin-2''-yl) phenoxy)pentane.

* * * * *